United States Patent

Horrobin et al.

[11] Patent Number: 5,508,307
[45] Date of Patent: Apr. 16, 1996

[54] METHOD FOR THE SAFE ADMINISTRATION OF FATTY ACID

[75] Inventors: David F. Horrobin; Catherine A. Scott, both of Guildford, England

[73] Assignee: Scotia Holdings PLC, Surrey, United Kingdom

[21] Appl. No.: 378,708

[22] Filed: Jan. 26, 1995

Related U.S. Application Data

[63] Continuation of Ser. No. 111,523, Aug. 25, 1993, abandoned.

[30] Foreign Application Priority Data

Aug. 25, 1992 [GB] United Kingdom ............... 9218064
Oct. 28, 1992 [GB] United Kingdom ............... 9222654

[51] Int. Cl.$^6$ .................................................. A61K 31/20
[52] U.S. Cl. ................................................... 514/560
[58] Field of Search ....................................... 514/560

[56] References Cited

U.S. PATENT DOCUMENTS 5,252,333  10/1993  Horrobin .................... 514/905

FOREIGN PATENT DOCUMENTS 0289204  11/1988  European Pat. Off. .

OTHER PUBLICATIONS

*Derwent Publications Ltd.,* London, GB: AN 91-152285 & JP-A-3 086 819 (Nippon Oils & Fats KK), 11 Apr. 1991 (Abstract).

*Cancer Reserach,* vol. 51, No. 22, 15 Nov. 1991, pp. 6025-6030, Cornelius et al: "Cytotoxic Effect of CIS-Parinaric Acid in Cultured Malignant Cells".

*Primary Examiner*—Raymond Henley, III
*Attorney, Agent, or Firm*—Nixon & Vanderhye

[57] ABSTRACT

Method of safe intravenous administration of fatty acid(s), and in particular the n-6 and n-3 series essential fatty acids and conjugated fatty acids, whereby the fatty acid(s) or a proportion thereof are administered in the form of lithium salts, and whereby the plasma lithium levels are regularly monitored to avoid haemolysis, preferably keeping the lithium level no higher than 0.7 millimolar in the long term and preferably also no higher than 0.4-0.5 millimolar in the first 24-48 hours or, where only a proportion of the fatty acids are administered as lithium salts, a corresponding proportion of said levels.

4 Claims, No Drawings

METHOD FOR THE SAFE ADMINISTRATION OF FATTY ACID

This is a continuation of application Ser. No. 08/111,523, filed Aug. 25, 1993, now abandoned.

The invention relates to a method for the safe intravenous administration of fatty acids, in particular the n-6 and n-3 series of fatty acids and conjugated fatty acids.

Fatty acids have a number of therapeutic actions. This is particularly true of the n-6 and n-3 series essential fatty acids. Different fatty acids may have desirable effects in a wide range of disorders including disorders of inflammation, in cancer, in infections and particularly viral infections, in psychiatric disorders, in cardiovascular disorders, in diabetes, in immunological disorders, in renal disorders, in reproductive disorders, in osteoporosis and disorders of calcium metabolism, and in skin disorders. Possible uses for fatty acid therapy have been described in the literature (e.g. in Horrobin D. F., Reviews in Contemporary Pharmacotherapy, volume 1, number 1; in "Omega-Essential Fatty Acids", edited by D.F. Horrobin, Wiley-Liss, New York, 1990; and in many previous patent applications by the applicant).

Although many different fatty acids have been proposed in therapy of various types, particular interest applies to the n-6 and n-3 series fatty acids either when used as the free fatty acid or as various derivatives such as salts, esters, glycerides, amides and phospholipids. The lithium salts of the fatty acids are of particular interest because they have properties which make them of particular value in a variety of situations see for example U.S. Pat. No. 4,328,243, EP 0 068 854 (U.S. Pat. No. 4,386,072), EP 0 085 579, EP 0 234 733 (U.S. Pat. Nos. 4,753,964 and 4,810,497), EP 0 289 204, EP 0 305 097, and UK 2 222 080, which discuss the use of lithium with EFA's in different forms including salts of lithium itself.

The pathways of conversion of the main series of polyunsaturated fatty acids in the body are as in Table 1 below:

TABLE 1

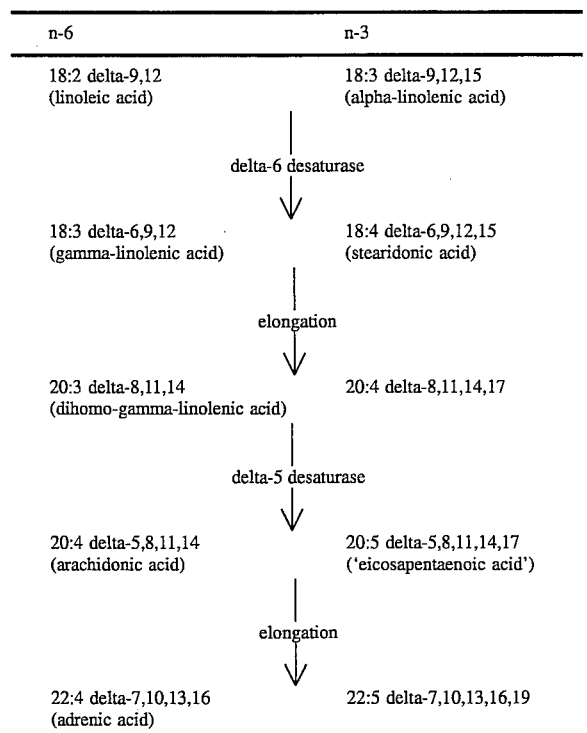

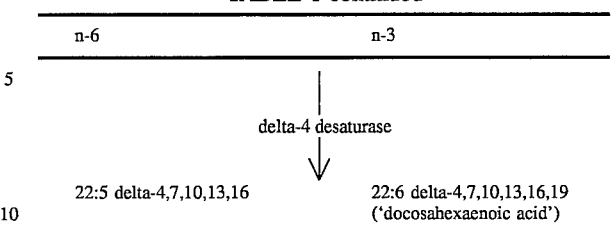

The above pathways are not normally reversible nor, in man, are n-3 and n-6 series acids interconvertible.

The acids, which in nature are of the all-cis configuration, are systematically named as derivatives of the corresponding octadecanoic, eicosanoic or docosanoic acids, e.g. delta-9,12-octadecadienoic acid or delta-4,7,10,13,16,19 docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

For some purposes it is desirable to get into the body the highest tolerable concentration of a fatty acid. This is particularly the case with cancer and with acute viral infections but can occur in many therapeutic situations. Certain fatty acids, in particular polyunsaturated fatty acids, and especially the n-6 and n-3 series fatty acids are able to kill cancer cells at concentrations which do not harm normal cells. Similar fatty acids are also able to kill viruses, in particular enveloped viruses, where they act in part by disrupting the lipid coat of the virus.

We and others have recently found that other fatty acids which have unsaturated double-bonds, notably conjugated fatty acids of chain length C-10 or greater, may also have selective actions in killing cancer cells at concentrations which do not harm normal cells (e.g. Corneillius A. S., Yerram N. R., Cratz D. A., Spector A. A., Cancer Research 51: 6025–6030, 1991). Conjugation is defined as a series of alternating single or double bonds in the carbon chain (e.g. Hopkins C Y, Topics in Lipid Chemistry 3:37–87, 1972). The double bonds may be in either the cis or the trans configuration; this is in contrast to the situation with the essential fatty acids in which all the double bonds must be in the cis configuration. The conjugated fatty acids may have two or more doubly unsaturated bonds but it appears that those with three or four such bonds may be particularly effective. Many fatty acids with this conjugated character istic are known (e.g. Hopkins). Patinatic acid (18:4, 9 cis, 11 trans, 13 trans, 15 cis) and alpha-eleostearic acid (18:3, 9 cis, 11 trans, 13 trans) are good examples. As with essential fatty acids it seems probable that the efficacy of these fatty acids against cancer cells depends on their unusually easy oxidation.

In these and other serious disease situations it is desirable to achieve a high concentration of the fatty acid in the body fluids for as long a time as possible. This can best be achieved by intravenous administration. However, at sufficiently high concentrations fatty acids and their salts disrupt membranes of all cells whether normal or abnormal. This is clearly a hazard and can make the fatty acids difficult to deliver intravenously.

We have been involved in the intravenous administration of fatty acids and their salts to animals and humans for a number of years. We have found that the damage to normal cells can readily be detected by the disruption of red cell membranes. Haemoglobin (Hb) in the blood is normally held entirely within the red cells and none is present in the plasma: because of this no haemoglobin is normally found in the urine. However, when a sufficient amount of a fatty acid is present in the blood, some of the red cells disintegrate, leaking haemoglobin into the blood and then the urine. This however represents a major health hazard and necessitates termination of the intravenous fatty acid infusion until haemoglobin can no longer be detected in the urine, when the infusion may be safely restarted at a lower dose.

The haemolysis is not readily preventable by controlling the administration of the fatty acid on a dose/kg basis. Different individuals metabolise the fatty acids in different ways and at different rates so that sometimes the haemolysis may occur at much lower infusion rates than expected whereas on other occasions the haemolysis does not occur even at very high doses, and although in theory the rate of fatty acid administration may be controlled by measuring the free fatty acid levels in the plasma we have not found this to be a practical method of monitoring the dose. The methodology is too laborious and not generally available in hospitals so that the doctor cannot get rapid feedback.

We have solved these problems by the use of the lithium salts of the essential fatty acids such as the salts of linoleic, gamma-linolenic, dihomo-gamma-linolenic, arachidonic, alpha-linolenic, stearidonic, eicosapentaenoic, docosapentaenoic and docosahexaenoic acids, though the method can be applied to any fatty acid, and in particular the conjugated fatty acids discussed earlier.

Because lithium is present in the blood normally only in trace amounts, any additional lithium is readily detected. Moreover, methods for lithium analysis such as flame photometry and atomic absorption spectrophotometry are very rapid and are readily available in every hospital. Therefore if the lithium salts of the fatty acids are used as a way of delivering the fatty acids to the body or at least a predetermined proportion thereof, the amount of fatty acid in the plasma can be readily and rapidly monitored by measuring the lithium levels.

Thus, the invention provides a method of safely administering fatty acid(s) intravenously, and in particular the n-6 and n-3 series essential fatty acids and conjugated fatty acids, whereby the fatty acid(s) or a proportion thereof are administered in the form of lithium salts, and whereby the plasma lithium levels are regularly monitored to avoid haemolysis, preferably keeping the lithium level no higher than 0.7 millimolar in the long term and preferably also no higher than 0.4–0.5 millimolar in the first 24–48 hours or, where only a proportion of the fatty acids are administered as lithium salts, a corresponding proportion of said levels.

The method of the invention is especially suited for use in the treatment of cancer, viral infections or other conditions mentioned herein.

Further, according to the invention, lithium salts of fatty acid(s), particularly the n-6 and n-3 series essential fatty acids and conjugated fatty acids are used in the preparation of a medicament suitable for use in monitored intravenous administration, in particular for the treatment of cancer or any of the other conditions referred to herein requiring maintenance of high plasma fatty acid levels, said medicament consituting an intravenous infusion medium or a material for incorporation in such a medium.

We have indeed found that this is a practical method of controlling fatty acid administration in clinical practice in a series of 12 patients with cancer. If, in the first two days of treatment lithium levels are monitored twice daily (or more frequently if desired) during an infusion of the lithium salts of the fatty acids, then we have found that haemolysis almost never occurs if the plasma lithium level remains below 0.4 to 0.5 millimolar. The rate of infusion can then be increased and if infusions last for more than 48 hours, haemolysis is highly unlikely to occur if the lithium level in plasma is kept below 0.7 millimolar. These guidelines enable fatty acids to be given intravenously in an entirely safe manner for an indefinite period of time. The use of lithium salts enables the fatty acids to be used easily by any doctor or nurse, since the safe levels can easily be monitored with feedback from the hospital laboratory in a matter of minutes if necessary.

In psychiatry, the target plasma concentrations of lithium in chronic oral use are 0.5–1.0 millimolar, sometimes going up to 1.5 millimolar. Them is relatively little risk of acute toxicity at concentrations below 2.0 millimolar at which central nervous symptoms become apparent. Chronic use for months or years at concentrations over 1.0 millimolar may cause renal damage but there is relatively little risk of this in the short term. There is thus no doubt that the limiting toxicity of the lithium-EFA salts is that of the fatty acids and not the lithium. This toxicity is primarily because of the detergent effects of the EFAs. If, however, lower doses of lithium are desired than indicated by giving the whole of the fatty acid as the lithium salt, it can be administered with only a proportion as the lithium salt, and the rest as other derivative(s) as mentioned herein, or as free fatty acid. The plasma lithium level is then monitored at a corresponding proportion of the 0.4 or 0.7 millimolar level.

The following example illustrates the application of the invention.

EXAMPLE

Lithium gamma-linolenate, eicosapentaenoate, dihomo-gamma-linolenate, arachidonate, docosahexaenoate, docosapentaenoate (n-3 or n-6), adrenate, linoleate, stearidonate, alpha-linolenate, parinarate, alpha-eleostearate or other appropriate fatty acid lithium salt is made up at 5–500 mg/ml, preferably 50–200 mg/ml, in an appropriate solution such as 20% ethanol in water or 0.9% saline, in sterile ampoules. Such ampoules are then added to appropriate conventional intravenous fluids such as 0.9% saline, or other appropriate intravenous fluid to achieve a final concentration of 1–100 mg/ml, preferably 5–20 mg/ml in the fluid to be administered. This final intravenous fluid is then slowly administered intravenously to a patient requiring maintenance of high plasma fatty acid levels, in order to deliver 1–5,000 mg/kg/day, preferably 50–250 mg/kg/day of the lithium salt to the patient. At, for example, 2h, 4h, 6h, 12h and 24h after starting the infusion or at 6, 8, 12, 24, 48 or 72 hourly thereafter, blood samples are taken from a vein which is not receiving the infusion, preferably from another limb, and the plasma lithium measured to ensure that it remains within the desired limits of 0.4 or 0.5 millimolar or 0.7 millimolar as above, or higher concentration if desired and if found in the particular patient not to lead to haemolysis.

We claim:

1. A method of safely administering fatty acid(s) intravenously, whereby the fatty acid(s) or a proportion thereof are administered in the form of lithium salts, and whereby the plasma lithium levels are regularly monitored by measurement of plasma lithium levels to avoid hemolysis arising from the presence of the fatty acids, keeping the lithium level and hence the fatty acid level no higher than 0.7 millimolar at the third day of treatment or, where only a proportion of the fatty acids are administered as lithium salts, a corresponding proportion of said level of 0.7 millimolar.

2. A method according to claim 1, wherein the lithium level is no higher than 0.4–0.5 millimolar in the first 24–48 hours of administration.

3. A method according to claim 1, wherein the fatty acid is an n-6 series essential fatty acid, an n-3 series essential fatty acid or a conjugated fatty acid.

4. A method according to claim 1, wherein the fatty acid(s) are selected from linoleic, gamma-linolenic, dihomo-gamma-linolenic, arachidonic, alpha-linolenic, stearidonic, eicosapentaenoic, docosapentaenoic, docosahexaenoic, parinaric and alpha-eleostearic acids.

* * * * *